United States Patent [19]

Iwayama et al.

[11] Patent Number: 4,467,129

[45] Date of Patent: Aug. 21, 1984

[54] CONVERSION OF XYLENES CONTAINING ETHYLBENZENE

[75] Inventors: Kazuyoshi Iwayama, Kamakura; Atsushi Ebitani, Kawasaki; Takehisa Inoue, Tokyo; Atsuo Kani, Zushi, all of Japan

[73] Assignee: Toray Industries, Inc., Tokyo, Japan

[21] Appl. No.: 444,306

[22] Filed: Nov. 24, 1982

[51] Int. Cl.$^3$ .............................................. C07C 5/22
[52] U.S. Cl. ................................. 585/481; 585/488; 585/489
[58] Field of Search ................ 585/481, 488, 489

[56] References Cited

U.S. PATENT DOCUMENTS

| | | |
|---|---|---|
| 3,281,482 | 10/1966 | Dvoretzky et al. ............ 585/481 |
| 3,281,483 | 10/1966 | Benesi et al. ................... 585/475 |
| 3,856,872 | 12/1974 | Morrison . |
| 3,856,873 | 12/1974 | Burress . |
| 4,218,573 | 8/1980 | Tabak et al. ................... 585/481 |
| 4,351,979 | 9/1982 | Chester et al. ................ 585/481 |

FOREIGN PATENT DOCUMENTS 45-21930 7/1970 Japan .

Primary Examiner—Curtis R. Davis
Attorney, Agent, or Firm—Stevens, Davis, Miller & Mosher

[57] ABSTRACT

Xylenes containing ethylbenzene are contacted with a catalyst comprising an acid type mordenite and a specific acid type zeolite such as, for example, ZSM-5, ZSM-8 or ZSM-11, in vapor phase in the presence of hydrogen, whereby there are performed deethylation of ethylbenzene and isomerization of xylenes.

11 Claims, No Drawings

CONVERSION OF XYLENES CONTAINING ETHYLBENZENE

BACKGROUND OF THE INVENTION

The present invention relates to a catalytic conversion process for xylenes containing ethylbenzene.

Among the xylenes, it is para-xylene that is in the greatest industrial demand at present, so the isomerization technique for converting ortho- and meta-xylenes which are in less demand into para-xylene is industrially important.

In general, industrially utilized xylenes are obtained by aromatic extraction and fractional distillation of reaction products from reforming or cracking of naphthas. But all of the crude xylenes thus obtained contain ethylbenzenes in addition to ortho-, meta- and para-xylenes. Therefore, ethylbenzenes is removed from such crude xylenes by some suitable means, and para-xylene is produced by the combination of separation step and isomerization step.

Ethylbenzene may be removed by direct separation thereof or by reaction thereof for conversion into a more useful compound. An example of the former is the distillation process wherein, however, it is necessary to perform an ultra-rectification because of a small difference in boiling point between ethylbenzene and xylenes, and this necessity results in increased equipment cost and running expenses. Thus, the distillation process is disadvantageous from the economic point of view. An example of the latter is a method wherein ethylbenzene is converted to xylenes by using a bifunctional catalyst comprising a platinum component and a solid acid component and at the same time there is performed isomerization of the xylenes. The method of removing ethylbenzene by the reaction is economically advantageous because it requires no special equipment. But a further improvement is desired because of problems involved therein, for example, platinum used in the above-mentioned bifunctional catalyst is a very expensive noble catalyst, and the conversion of ethylbenzene is restricted by a thermodynamic equilibrium relation between ethylbenzene and xylene isomers.

As the method for overcoming the above-mentioned problems, an increasing attention has recently been placed on a conversion process for ethylbenzene into benzene and ethane by using a catalyst comprising a solid acid component and a hydrogenation component. The hydrodealkylation reaction of ethylbenzene into benzene and ethane has features such that the improvement of conversion is relatively easy because the reaction scarcely undergoes thermodynamic restrictions, and that the resulting benzene is easily separable by the distillation process because of a large difference in boiling point from xylenes and has a high added value as a raw material for synthetic fibers and synthetic resins. As a catalyst for allowing such reactions to proceed efficiently, the present inventors have proposed a mordenite catalyst containing rhenium and/or phosphorus or this mordenite catalyst further containing molybdenum, tungsten and/or vanadium, previously in Japanese Laid Open Patent Publication Nos. 9727/1982, 64623/1982 and 134423/1982. But, to make this reaction more efficient, it is desirable to further improve the catalyst activity and selectivity.

SUMMARY OF THE INVENTION

It is an object of the present invention to overcome the foregoing disadvantages of the prior art.

It is another object of the present invention to provide a conversion process for xylenes containing ethylbenzene.

It is a further object of the present invention to provide a process for deethylation of ethylbenzene into benzene and simultaneous isomerization of xylenes efficiently.

The above-mentioned objects of the present invention can be achieved by contacting xylenes containing ethylbenzene with a catalyst comprising an acid type mordenite and an acid type zeolite which exhibits the X-ray diffraction pattern shown in Table 1 below, in the presence of hydrogen.

TABLE 1

| d (Å) |
| --- |
| 11.2 ± 0.2 |
| 10.1 ± 0.2 |
| 3.86 ± 0.08 |
| 3.72 ± 0.08 |
| 3.66 ± 0.08 |

DESCRIPTION OF THE PREFERRED EMBODIMENT

As the mordenite used in the present invention, there may be employed any of synthetic and natural zeolites having the crystal structure of mordenite. Of course, a mixture of synthetic and natural zeolites may be used. The mordenite can be produced, for example, by the process disclosed in U.S. Pat. No. 3,436,174 or European Laid Open Patent Publication No. 57,016.

As the zeolite used in the present invention, exhibiting the X-ray diffraction pattern shown in Table 1, there may be employed, for example, ZSM-5 disclosed in U.S. Pat. No. 3,894,106, ZSM-8 disclosed in British Patent No. 1,334,243, ZSM-11 disclosed in U.S. Pat. No. 3,709,979, Zeta 3 disclosed in German Laid Open Patent Publication No. 2,548,695, zeolite prepared without adding an organic substance into reaction mixture, as disclosed in U.S. Pat. No. 4,257,885, or zeolite prepared by adding a carboxyl group-containing organic compound into reaction mixture, as disclosed in European Laid Open Patent Publication No. 57,016.

Without being restricted to those just exemplified above, any other zeolites are employable provided they have a structural characteristic exhibiting the X-ray diffraction pattern shown in Table 1. But, zeolites which exhibit the X-ray diffraction pattern shown in Table 2 below are more preferable.

TABLE 2

| d (Å) | d (Å) |
| --- | --- |
| 11.2 ± 0.2 | 4.27 ± 0.08 |
| 10.1 ± 0.2 | 3.86 ± 0.08 |
| 6.37 ± 0.1 | 3.75 ± 0.08 |
| 6.00 ± 0.1 | 3.72 ± 0.08 |
| 5.71 ± 0.1 | 3.66 ± 0.08 |
| 5.58 ± 0.1 | 3.00 ± 0.05 |
| 4.37 ± 0.08 | 2.00 ± 0.05 |

The $SiO_2/Al_2O_3$ mole ratio of the zeolite is preferably not less than 10, particularly in the range of 20 to 200 and further 30 to 150.

The weight ratio between the zeolite (hereinafter referred to as the zeolite (a)) which exhibits the X-ray diffraction pattern shown in Table 1, and the mordenite, both contained in the catalyst used in the present invention, is preferably in the range of 1% to 50%, more preferably 5% to 30%, in terms of percentage by weight of the zeolite (a) based on the total weight of both zeolites, i.e. the zeolite (a) and the mordenite. The catalyst may contain an additional component or components, for example, an inert alumina, other than the two kinds of zeolites described above.

The mordenite and the zeolite (a), before their use in the invention, should be treated into acid type. Acid type zeolites, as well known, have hydrogen ions as cations, and they are obtained usually by ion-exchanging at least part of alkali metal ions and/or alkaline earth metal ions of zeolites which contain those exchangeable cations, with hydrogen ions and/or ammonium cations as a hydrogen ion precursor. Generally, the ion-exchange treatment is carried out by using an aqueous solution which contains an acid and/or an ammonium salt. In this case, both inorganic and organic acids are employable, but the use of inorganic acids is more common. Examples of inorganic acids include hydrochloric, nitric, phosphoric and carbonic acids. Of course, there may be used other inorganic acids provided they contain hydrogen ion. Preferred concentrations of acids vary according to the kind of acids used, so it is difficult to absolutely define such concentrations, but care should be exercised to avoid destruction of the mordenite structure.

Examples of ammonium salts which may be used include inorganic ammonium salts such as ammonium nitrate, ammonium chloride, ammonium sulfate, ammonium carbonate and aqueous ammonia, as well as ammonium salts of organic acids such as ammonium formate, ammonium acetate and ammonium citrate, with inorganic ammonium salts being preferred. Ammonium salts are used as a solution of preferably 0.05 to 4N, more preferably about 0.1 to 2N.

As the method of such ion-exchange treatment for the zeolites using the acid and/or ammonium salt solution, both batch method and flow method are employable preferably. In case the treatment is made by the batch method, the solid-liquid ratio should be at least a ratio at which the zeolites can fully contact the liquid, preferably about 1 l/kg or more. A treatment time from about 0.1 to 72 hours is sufficient, preferably from about 0.5 to 24 hours, and a treatment temperature below the boiling point is sufficient, but preferably heat is applied to accelerate the ion-exchange rate. In case the flow method is to be followed, there may be adopted the fixed-bed process and the fluidized-bed process, but it is necessary to give consideration so that there may not occur fluid channelling or the ion exchange treatment may not become non-uniform.

The zeolites after subjected to the ion exchange treatment are washed with water, preferably with distilled water, according to either the batch method or the flow method. In this way, hydrogen ions or ammonium ions as a hydrogen ion precursor are introduced in the zeolites.

In the case of the zeolites ZSM-5, ZSM-8 and ZSM-11, since an organic nitrogen-containing cation is used at the time of their production, they can be changed into acid type zeolites by allowing the said organic nitrogen-containing cation to decompose upon calcining for conversion thereof into hydrogen ion, even without application of the ion exchange treatment using the acid and/or ammonium salt solution.

The ratio of hydrogen ions in the catalyst to the entire exchangeable cations is preferably in the range of 30% to 90%, more preferably 40% to 80%, in terms of gram ion equivalent. A too low ratio is not desirable because it would cause deterioration of the reaction activity. A too high ratio is not desirable, either, because a disproportionation reaction as a side reaction would be accelerated although the reaction activity would become higher. The zeolites thus ion-exchanged with hydrogen ions, namely, the proton type zeolites, if further subjected to heat treatment at a high temperature, become so-called decationized zeolites. But, decationized zeolites and proton type zeolites are not always distinguishable clearly from each other and are often used indiscriminately. The acid type as referred to herein include decationized type.

If only the zeolites in the catalyst used in the present invention are acid type zeolites, the remaining cations may be various cations. Particularly, alkaline earth metals are preferred because they are effective in improving the reaction selectivity. To let the zeolites contain alkaline earth metal ions, it is necessary to perform an ion exchange for introducing such ions in addition to the ion exchange for introducing hydrogen ions and/or ammonium ions as a hydrogen ion precursor. The ion exchange for introducing alkaline earth metal ions is carried out by treating the zeolites with a solution which contains a compound of an alkaline earth metal. Preferred alkaline earth metals are magnesium, calcium, strontium and barium.

In case it is necessary to perform the ion exchange for introducing alkaline earth metal ions, this ion exchange treatment may be conducted separately from the ion exchange treatment for introducing ammonium ions, or both treatments may be carried out at a time.

According to a particularly preferred ion-exchanging method in the preparation of the catalyst used in the invention, first the ion exchange treatment for introducing alkaline earth metal ions is conducted and then the same treatment for introducing hydrogen ions and/or ammonium ions as a hydrogen ion precursor is performed by a liquid recycle type batch process.

In the reaction of the invention using the catalyst thus prepared, ethylbenzene is hydrodealkylated for conversion to benzene and ethane. Therefore, it is preferable that the catalyst used in the invention contain a component having a certain specific hydrogenation activity. Examples of such component include nickel, cobalt, rhenium, molybdenum, tungsten and vanadium. Noble metals such as platinum and palladium are not preferable in the reaction of the invention. If a platinum-supported catalyst is used in the reaction of the invention, there occurs a hydrogenation reaction at the benzene nuclei of the xylenes because the hydrogenation activity of platinum is too strong, and therefore such catalyst is not desirable. A preferred amount of rhenium to be added ranges from 0.005 to 3%, more preferably 0.02 to 0.5%, by weight as the rhenium element based on the weight of the entire catalyst. A preferred amount of molybdenum, tungsten or vanadium to be added ranges from 0.1 to 10%, more preferably 0.2 to 5%, by weight as the element based on the weight of the entire catalyst. A too small amount is not effective, while a too large amount causes side reaction, and thus both such amounts are not desirable.

As the method for adding such metal to the other catalyst components, there may be adopted, for example, a kneading method, impregnation method and a method of physically mixing powders with each other. For adding the metal element by the kneading method, a compound of the element may be added and kneaded simultaneously with mixing of the mordenite and the zeolite (a) in their granulation. According to the impregnation method, usually, it is possible to support the element by impregnating the zeolites after granulation into a solution containing a compound of the element, followed by draining and drying. In the process of the present invention, the impregnation method is preferred. As the solvent for dissolving the compound of the element, there may be used organic solvents such as alcohols, not to mention water. The amount of the element to be added can be adjusted by suitably selecting the concentration of the compound of the element in the solution.

Examples of compounds of the element which may be used in the invention include, with respect to rhenium, rhenium oxide, perrhenic acid, ammonium perrhenate and rhenium sulfide; with respect to molybdenum, ammonium molybdate, ammonium paramolybdate, ammonium phosphomolybdate, molybdic acid, molybdenum oxide, molybdenum sulfide and molybdates; and with respect to tungsten, ammonium tungstate, ammonium phosphotungstate, tungsten oxide, tungsten sulfide, tungsten carbide and tungstates.

Either a fixed bed or a fluidized bed may be used as a reaction apparatus in the present invention, but the former is preferred because of simpler construction and easier operation. In the fixed bed process, it is preferable from the standpoint of catalyst effectiveness factor that the particle diameter of the catalyst be as small as possible, provided a too small particle diameter is not desirable because it would cause an increased pressure drop. That is, there exists a preferable range of catalyst diameter, which is from 0.05 to 10 mm, more preferably from 0.1 to 2 mm. As the case may be, molding is needed in order for the catalyst to have such a preferred range of particle diameter, for example, compression molding and extrusion. And in order to improve the moldability or impart strength to the catalyst, there may be used a binder, though it goes without saying that the use of binder may be omitted if molding is attainable to a satisfactory extent without the binder. Preferred examples of the binder include natural clays such as kaolin, bentonite, montmorillonite and acid clay as well as synthetic products such as silica sol, alumina sol and alumina gel. The amount of the binder to be added is not more than 70%, preferably not more than 20%, by weight.

The catalyst used in the present invention is prepared basically through the steps of mixing the two zeolite components, molding and treatment into the acid type, the order of which steps may be selected suitably. For example, both zeolite powders may each be treated into the acid type, then mixed and thereafter molded to obtain the catalyst, or both zeolite powders may be molded and treated into the acid type each independently and then mixed to obtain the catalyst.

As described above, the catalyst thus prepared is dried and subsequently calcined before its use. The drying is performed at 50° to 250° C. for over 0.1 hour, preferably 0.5 to 48 hours, and the calcination is performed at 300° to 700° C. for over 0.1 hour, preferably at 400° to 600° C. for 0.5 to 24 hours. By this calcination the ammonium ions introduced in the zeolites by the ion exchange treatment are converted to hydrogen ions, which in turn are converted to the decationized type as the calcination temperature increases, and the catalyst in such a form is also employable effectively.

The catalyst prepared in the manner described above is used under the following reaction conditions. The operating temperature ranges from 300° to 600° C., preferably from 350° to 550° C., and the operating pressure ranges from atmospheric pressure to 100 kg/cm$^2$.G, preferably from atmospheric pressure to 50 kg/cm$^2$.G. The time factor W/F (g-cat.hr/g-mol feed stock, W: catalyst weight, F: mol feed stock per hour) which means the contact time of reaction is in the range of 0.1 to 200, preferably 1 to 100. It is essential that hydrogen is present in the reaction system. If the hydrogen concentration is too low, the dealkylation reaction of ethylbenzene will not proceed to a sufficient extent and a carbonaceous component will be deposited on the catalyst thus resulting in deterioration of the catalyst activity with the lapse of time. A too high concentration of hydrogen is not desirable, either, because it would cause an increase of hydrocracking reaction. That is, there exists a preferable range of hydrogen concentration, which is 1 to 50, preferably 3 to 30, in terms of mol ratio of hydrogens to feed stock ($H_2$/F).

As the feed stock there is used a mixture of xylenes containing ethylbenzenes, wherein the concentration of ethylbenzene is not specially limited. The concentration of para-xylene in the xylene mixture is preferably below the thermodynamic equilibrium concentration, but it is of course possible, as one mode of use in the present invention, to use as the feed stock a xylene mixture containing para-xylene of the thermodynamic equilibrium concentration with a view to decreasing the concentration of ethylbenzene.

The feed stock may contain other aromatic components, e.g. benzene, toluene, trimethylbenzene, ethyltoluene, diethylbenzene, ethylxylene, provided their concentrations should be in a low range.

The following examples are given to further illustrate the present invention.

EXAMPLE 1

14.7 g. of a solid sodium hydroxide and 10.5 g. of tartaric acid were dissolved in 351 g. of water, then 5.24 g. of a sodium aluminate solution was added to prepare a homogeneous solution. To this mixed solution was then added, slowly with stirring, 66.0 g. of silicic acid powder available commercially as white carbon to prepare a homogeneous, slurried, aqueous reaction mixture having the following composition in terms of mol ratios:

| | |
|---|---|
| $SiO_2/Al_2O_3$ | 100 |
| $H_2O/SiO_2$ | 20 |
| $OH^-/SiO_2$ | 0.24 |
| $TA/Al_2O_3$ | 7 |

(TA: Tartaric acid)

The mixture was charged into an autoclave having a capacity of 500 ml. and the autoclave was closed. Then, heating was made to 160° C. with stirring and crystallization was allowed to take place for 72 hours. Then, after cooling, the product was taken out of the autoclave, washed with distilled water and filtered until the pH was almost neutral, and then dried overnight at 110°

C. The product thereby obtained was a zeolite having the X-ray diffraction pattern shown in Table 3. Chemical composition of the zeolite upon analysis proved to be 1.3 $Na_2O\cdot Al_2O_3$, 48.7 $SiO_2$ in a dehydrated state.

TABLE 3

| d (Å) | X-ray diffraction pattern 100 I/Io | d (Å) | 100 I/Io |
|---|---|---|---|
| 11.18 | 39 | 3.82 | 80 |
| 10.10 | 32 | 3.76 | 41 |
| 9.82 | 13 | 3.73 | 47 |
| 7.49 | 3 | 3.66 | 29 |
| 6.75 | 5 | 3.49 | 5 |
| 6.41 | 10 | 3.45 | 14 |
| 6.04 | 14 | 3.36 | 6 |
| 5.73 | 11 | 3.32 | 14 |
| 5.60 | 12 | 3.06 | 14 |
| 5.40 | 3 | 3.00 | 13 |
| 5.18 | 2 | 2.87 | 4 |
| 5.06 | 5 | 2.74 | 5 |
| 5.01 | 6 | 2.62 | 4 |
| 4.64 | 6 | 2.49 | 8 |
| 4.39 | 8 | 2.02 | 10 |
| 4.29 | 14 | 2.00 | 11 |
| 4.11 | 13 | 1.92 | 3 |
| 4.02 | 7 | 1.88 | 5 |
| 3.86 | 100 | | |

EXAMPLE 2

7.49 g. of a solid sodium hydroxide and 18.8 g. of tartaric acid were dissolved in 325 g. of water, then 52.4 g. of a sodium aluminate solution was added to prepare a homogeneous solution. To this mixed solution was then added, slowly with stirring, 66.0 g. of silicic acid powder to prepare a homogeneous, slurried, aqueous reaction mixture having the following composition in terms of mol ratios:

| | |
|---|---|
| $SiO_2/Al_2O_3$ | 10 |
| $H_2O/SiO_2$ | 20 |
| $OH^-/SiO_2$ | 0.275 |
| $TA/Al_2O_3$ | 1.25 |

(TA: tartaric acid)

The mixture was charged into an autoclave having a capacity of 500 ml. and the autoclave was closed. Then, heating was made to 160° C. with stirring and crystallization was allowed to take place for 48 hours. Then, after cooling, the product was taken out of the autoclave, washed with distilled water and filtered until the pH was almost neutral, and then dried overnight at 110° C. The product thereby obtained as a mordenite type zeolite having the X-ray diffraction pattern shown in Table 4. Chemical composition of the zeolite upon analysis proved to be 0.96 $Na_2O\cdot Al_2O_3$, 9.7 $SiO_2$ dihydrated state.

TABLE 4

| d (Å) | X-ray diffraction pattern 100 I/Io | d (Å) | 100 I/Io |
|---|---|---|---|
| 13.86 | 22 | 3.24 | 39 |
| 10.42 | 7 | 3.21 | 47 |
| 9.18 | 55 | 3.17 | 8 |
| 6.64 | 34 | 3.12 | 4 |
| 6.45 | 26 | 2.90 | 27 |
| 6.13 | 10 | 2.72 | 2 |
| 5.85 | 17 | 2.64 | 2 |
| 5.15 | 3 | 2.56 | 8 |
| 5.08 | 3 | 2.52 | 14 |
| 4.55 | 38 | 2.47 | 4 |
| 4.16 | 4 | 2.44 | 4 |
| 4.01 | 77 | 2.28 | 2 |
| 3.86 | 9 | 2.23 | 3 |
| 3.78 | 13 | 2.16 | 2 |
| 3.65 | 3 | 2.04 | 8 |
| 3.55 | 11 | 1.96 | 8 |
| 3.49 | 100 | 1.92 | 3 |
| 3.40 | 63 | 1.88 | 8 |
| 3.30 | 10 | | |

EXAMPLE 3

2.2 g. of aluminum sulfate ($Al_2(SO_4)_3\cdot 18H_2O$), 11.3 g. of sulfuric acid and 15 g. of n-propylamine were dissolved in 231 g. of water, then 135 g. of sodium silicate No. 3 was added slowly with stirring to prepare as homogeneous a gel-like slurry as possible. The slurry was charged into an autoclave having a capacity of 500 ml. and the autoclave was closed. Crystallization was allowed to take place at 160° C. for 72 hours with stirring. Then, after cooling, the product was washed with distilled water and filtered. The water-washing and filtration were repeated until the washing was almost neutral, followed by drying overnight at about 110° C. The product thereby obtained was zeolite ZSM-5 containing organic ammonium cations with a $SiO_2/Al_2O_3$ mol rato of 137 and having the X-ray diffraction pattern shown in Table 5.

TABLE 5

| d (Å) | X-ray diffraction pattern 100 I/Io | d (Å) | 100 I/Io |
|---|---|---|---|
| 11.07 | 60 | 3.48 | 5 |
| 10.01 | 36 | 3.44 | 12 |
| 9.72 | 12 | 3.35 | 7 |
| 7.45 | 2 | 3.31 | 11 |
| 6.71 | 6 | 3.25 | 4 |
| 6.37 | 11 | 3.14 | 3 |
| 6.00 | 11 | 3.05 | 9 |
| 5.70 | 9 | 2.99 | 11 |
| 5.58 | 9 | 2.94 | 5 |
| 5.36 | 2 | 2.86 | 3 |
| 5.14 | 3 | 2.78 | 2 |
| 5.03 | 4 | 2.73 | 5 |
| 4.98 | 6 | 2.68 | 2 |
| 4.88 | 1 | 2.61 | 4 |
| 4.62 | 7 | 2.51 | 3 |
| 4.36 | 9 | 2.49 | 5 |
| 4.26 | 14 | 2.42 | 3 |
| 4.09 | 5 | 2.39 | 3 |
| 4.01 | 6 | 2.01 | 9 |
| 3.85 | 100 | 1.99 | 9 |
| 3.81 | 66 | 1.95 | 3 |
| 3.74 | 34 | 1.92 | 3 |
| 3.71 | 46 | 1.87 | 3 |
| 3.65 | 25 | | |

EXAMPLES 4–7

10 parts by weight (on absolute dry basis) powder of the crystalline aluminosilicate zeolite prepared in Example 1 was mixed with 45 parts by weight (on absolute dry basis) of a commercially available synthetic sodium type mordenite "Zeolon 100-NA" powder manufactured by Norton Company and 45 parts by weight (on absolute dry basis) of alumina powder as a diluent. Then, 15 parts by weight (as $Al_2O_3$) of alumina sol as a binder was added to the powder mixture. After kneading, the kneaded mass was extruded through a screen of 1 mm-φ. After the extrusion, the molded particles were dried overnight at about 110° C., then classified to 12-24 mesh and thereafter calcined in a muffle furnace at 500° C. for 2 hours. This molded product upon analysis proved to contain 1.06 meq/g of exchangeable sodium.

100 g. (on absolute dry basis) of the molded product was dipped in a solution of 10 g. ammonium chloride dissolved in 200 ml. of distilled water and ion-exchanged with ammonium ions for about 1 hour with stirring at times in a water bath at about 90° C., then thoroughly washed with distilled water and dried overnight at about 110° C. The so-treated product upon analysis proved to contain 0.703 and 0.297 meq/g of exchangeable ammonium and sodium, respectively. It was then calcined in a muffle furnace at 500° C. for 2 hours. The catalyst thus prepared will be referred to hereinafter as catalyst "A".

On the other hand, 20 g. (on absolute dry basis) of a likewise treated product after going through the ion exchange with ammonium ions and subsequent drying was impregnated in 40 ml. of an aqueous perrhenic acid containing 0.02 g. of rhenium as metal and allowed to stand for 30 minutes at room temperature, then allowed to drain and dried overnight at about 110° C. The dried product was then calcined in a muffle furnace at 500° C. for 2 hours. The catalyst thus prepared will be referred to hereinafter as catalyst "B".

Using an aqueous ammonium molybdate solution containing 0.20 g. of molybdenum as metal in place of the aqueous perrhenic acid solution, a catalyst was prepared in the same way, which will be referred to hereinafter a catalyst "C".

Furthermore, using an aqueous ammonium tungstate solution containing 0.20 g. of tungsten as metal in place of the aqueous perrhenic acid solution, a catalyst was prepared in the same way, which will be referred to hereinafter as catalyst "D".

Then, using the catalysts A, B, C and D, feed stocks each comprising ethylbenzene and xylenes were treated under the conditions shown in Table 6. The results are as set out in the same table.

EXAMPLES 8-11

7.5 parts by weight (on absolute dry basis) of the zeolite powder prepared in Example 1 and 92.5 parts by weight (on absolute dry basis) of the mordenite type zeolite powder prepared in Example 2 were mixed together, then 15 parts by weight (as $Al_2O_3$) of alumina sol as a binder was added to the powder mixture. After kneading, the kneaded mass was extruded through a screen of 1 mm-$\phi$, then the molded particles were dried overnight at about 110° C. and subsequently classified to 12-24 mesh, followed by calcining in a muffle furnace at 500° C. for 2 hours. This molded product upon analysis proved to contain 2.07 meq/g of exchangeable sodium.

40 g. (on absolute dry basis) of the molded product was dipped in a solution of 4.0 g. ammonium chloride dissolved in 80 ml. of distilled water and ion-exchanged with ammonium ions for about 1 hour with stirring at times in a water bath at about 90° C., then thoroughly washed with distilled water and dried overnight at about 110° C. The so-treated product upon analysis proved to contain 1.26 and 0.70 meq/g of exchangeable ammonium and sodium, respectively. It was then calcined in a muffle furnace at 500° C. for 2 hours. The catalyst thus prepared will be referred to hereinafter as catalyst "E".

On the other hand, 40 g. (on absolute dry basis) of the molded product was dipped in 80 ml. of an aqueous solution containing 5% by weight of calcium nitrate and ion-exchanged for about 1 hour with stirring at times on a hot water bath at about 90° C. This treatment with the calcium nitrate solution was repeated three times. Thereafter, the so-treated product was washed thoroughly with distilled water, then dipped in 180 ml. of an aqueous solution containing 4.0 g. of ammonium chloride and treated for about 1 hour with occasional stirring in a water bath at about 90° C., followed by thorough washing with distilled water and subsequent drying overnight at about 110° C. The treated product upon analysis proved to contain 1.00, 0.89 and 0.13 meq/g of exchangeable ammonium, calcium and sodium, respectively. 20 g. (on absolute dry basis) of the treated product was impregnated in 40 ml. of an aqueous perrhenic acid solution containing 0.02 g of rhenium as metal and allowed to stand for 30 minutes at room temperature, followed by calcining in a muffle furnace at 500° C. for 2 hours. The catalyst thus prepared will be hereinafter referred to as catalyst "F".

Furthermore, 40 g. (on absolute dry basis) of the molded product was treated using magnesium nitrate in place of calcium nitrate and subsequently treated with the aqueous ammonium chloride solution and the aqueous perrhenic acid in the same way as above to prepare a catalyst, which will be referred to hereinafter as catalyst "G".

Using strontium nitrate in place of calcium nitrate, a catalyst was prepared in the same manner as above, which will be referred to hereinafter as catalyst "H".

A conversion reaction of xylenes containing ethylbenzene was carried out using the catalysts E, F, G and H under the conditions shown in Table 6. The results are as set out in the same table.

EXAMPLES 12 AND 13

40 parts by weight (on absolute dry basis) of the zeolite ZSM-5 powder prepared in Example 3 and 60 parts by weight (on absolute dry basis) of the mordenite type zeolite powder prepared in Example 2 were mixed together, then 15 parts by weight (as $Al_2O_3$) of alumina sol as a binder was added to the powder mixture. After kneading, the kneaded mass was extruded through a screen of 1 mm-$\phi$, then the molded particles were dried overnight at about 120° C. and thereafter classified to 12-24 mesh, followed by calcining in a muffle furnace at 500° C. for 2 hour. 40 g. (on absolute dry basis) of this molded product was dipped in a solution of 6.0 g. ammonium chloride dissolved in 80 ml. of distilled water and ion-exchanged with ammonium ions for about 1 hour with occasional stirring in a water bath at about 90° C., followed by thorough washing with distilled water, drying overnight at about 110° C. and subsequent calcining in a muffle furnace at 500° C. for 2 hours. The catalyst thus prepared will be referred to hereinafter as catalyst "I".

On the other hand, 40 g. (on absolute dry basis) of the molded product was dipped in 80 ml. of an aqueous solution containing 5% by weight of magnesium nitrate and ion-exchanged for about 1 hour with occasional stirring in a water bath at about 90° C. This treatment with the aqueous magnesium nitrate solution was repeated five times. Thereafter, the so-treated product was washed thoroughly with distilled water, then dipped in 80 ml. of an aqueous solution containing 6.0 g. of ammonium chloride and ion-exchanged for about 1 hour with occasional stirring in a water bath at about 90° C., followed by thorough washing with distilled water and subsequent drying overnight at about 110° C. Exchangeable ammonium, magnesium and sodium contents upon analysis proved to be 0.82, 0.45 and 0.10 meq/g, respectively. 20 g. (on absolute dry basis) of this treated product was impregnated in 40 ml. of an aqueous perrhenic acid solution containing 0.02 g. of rhenium as metal and allowed to stand for 30 minutes at room temperature, then allowed to drain and dried overnight at about 110° C., then calcined in a muffle furnace at 500° C. for about 2 hours. The catalyst thus prepared will be referred to hereinafter as catalyst "J".

Using the catalysts I and J, a conversion reaction of xylenes was carried out under the conditions shown in Table 7. The results are as set out in the same table.

EXAMPLE 14

100 g. (on absolute dry basis) of the mordenite type zeolite powder prepared in Example 2 was dipped in 500 ml. of an aqueous solution containing 5.0% by weight of calcium nitrate and ion-exchanged for about 1 hour with occasional stirring in a water bath at about 90° C., then filtered and again subjected to the ion exchange treatment with the aqueous calcium nitrate solution, which operation was repeated five times, followed by thorough washing with distilled water. 50 g. (on absolute dry basis) of the mordenite type zeolite powder prepared in Example 2 thus ion-exchanged with calcium ions was dipped in an aqueous solution containing 5.0 g. of ammonium chloride and ion-exchanged with ammonium ions for about 1 hour with occasional stirring in a water bath at about 90° C., followed by thorough washing with distilled water and subsequent drying overnight at about 110° C.

30 g. (on absolute dry basis) powder of this mordenite type zeolite thus ion-exchanged with the aqueous ammonium chloride solution was mixed with 20 g. (on absolute dry basis) of the ZSM-5 powder prepared in Example 3. To this powder mixture were added 75 g. of alumina sol ($Al_2O_3$ content: 10 wt.%) as a binder and 10 ml. of an aqueous perrhenic acid solution containing 0.06 g. of rhenium as metal, followed by kneading. The kneaded mass was extruded through a screen of 1 mm-$\phi$, then the molded particles were dried overnight at about 110° C. and then classified to 12-24 mesh, followed by calcining in a muffle furnace at 500° C. for 2 hours. The catalyst thus prepared will be referred to hereinafter as catalyst "K".

Using the catalyst K, a conversion reaction of xylenes containing ethylbenzene was carried out under the conditions shown in Table 7. The results are as set out in the same table.

COMPARATIVE EXAMPLES 1 AND 2

60 parts by weight (on absolute dry basis) of the mordenite type zeolite powder prepared in Example 2 and 40 parts by weight (on absolute dry basis) of alumina powder as a diluent were mixed together, then to this powder mixed was added 15 parts by weight (as $Al_2O_3$) of alumina sol as a binder, followed by kneading. The kneaded mass was extruded through a screen of 1 mm-$\phi$, then the molded particles were dried overnight at about 110° C. and then classified to 12-24 mesh, followed by calcining in a muffle furnace at 500° C. for 2 hours. 20 g. (on absolute dry basis) of this molded product was dipped in 40 ml. of an aqueous solution containing 2.0 g. of ammonium chloride and ion-exchanged with ammonium ions for about 1 hour with occasional stirring in a water bath at about 90° C., then washed thoroughly with distilled water and dried overnight at about 110° C., followed by calcining in a muffle furnace at 500° C. for 2 hours. The catalyst thus prepared will be referred to hereinafter as catalyst "M".

40 parts by weight (on absolute dry basis) of the ZSM-5 powder prepared in Example 3 and 60 parts by weight (on absolute dry basis) of alumina powder as a diluent were mixed together, then to this powder mixture was added 15 parts by weight (as $Al_2O_3$) of alumina sol as a binder, followed by kneading. The kneaded mass was extruded through a screen of 1 mm-$\phi$, then the molded particles were dried overnight at about 110° C. and then classified to 12-24 mesh, followed by calcining in a muffle furnace at 500° C. for 2 hours. This molded product was treated with the aqueous ammonium chloride solution in the same way as above to prepare a catalyst, which catalyst will be referred to hereinafter as catalyst "L".

Using the catalysts L and M, a conversion reaction of xylenes containing ethylbenzene was carried out under the conditions shown in Table 7. The results are as set out in the same table. Reference to Table 7 shows that the caatalyst L affords a high ethylbenzene conversion but a low isomerization to para-xylene and that the catalyst M affords only a low ethylbenzene conversion.

TABLE 6

Evaluation of various catalysts

| Item | | | Example 4 | Example 5 | Example 6 | Example 7 | Example 8 | Example 9 | Example 10 | Example 11 |
|---|---|---|---|---|---|---|---|---|---|---|
| Catalyst | | | A | B | C | D | E | F | G | H |
| Reaction Conditions | Reaction Temperature (°C.) | | 400 | 400 | 400 | 400 | 400 | 400 | 400 | 400 |
| | Reaction Pressure ($kg/cm^2 \cdot G$) | | 12 | 12 | 12 | 12 | 12 | 12 | 12 | 12 |
| | $H_2/F$ (mol/mol) | | 4 | 4 | 4 | 4 | 4 | 4 | 4 | 4 |
| | W/F (g-cat · hr/g-mol) | | 30 | 30 | 30 | 30 | 30 | 30 | 30 | 30 |
| Reaction Products | $C_7^-$ wt. % | (Feed stock) 2.12 | 2.64 | 2.93 | 2.79 | 1.56 | 2.17 | 2.06 | 2.34 |
| | BZ | | 5.52 | 6.55 | 6.95 | 6.54 | 4.66 | 5.89 | 5.30 | 5.55 |
| | TOL | | 2.07 | 2.13 | 2.72 | 2.55 | 1.99 | 1.52 | 1.89 | 1.61 |
| | EB | 19.06 | 9.33 | 8.94 | 7.95 | 8.34 | 10.86 | 10.15 | 10.69 | 10.37 |
| | PX | 2.66 | 17.87 | 18.27 | 18.26 | 18.24 | 18.10 | 18.22 | 18.20 | 17.92 |
| | MX | 55.48 | 40.94 | 41.34 | 41.16 | 41.05 | 41.26 | 41.99 | 41.65 | 41.80 |
| | OX | 22.80 | 18.12 | 18.03 | 17.73 | 17.68 | 18.20 | 18.75 | 18.45 | 18.91 |
| | ET | | 0.57 | 0.26 | 0.29 | 0.32 | 0.38 | 0.21 | 0.31 | 0.27 |
| | TMB | | 1.12 | 1.10 | 1.30 | 1.33 | 0.91 | 0.56 | 0.69 | 0.59 |
| | DEB | | 1.72 | 0.41 | 0.41 | 0.76 | 1.66 | 0.32 | 0.42 | 0.33 |
| | EX | | 0.61 | 0.34 | 0.31 | 0.39 | 0.42 | 0.21 | 0.33 | 0.31 |

TABLE 6-continued

| | Evaluation of various catalysts | | | | | | | |
|---|---|---|---|---|---|---|---|---|
| Item | Example 4 | Example 5 | Example 6 | Example 7 | Example 8 | Example 9 | Example 10 | Example 11 |
| Catalyst | A | B | C | D | E | F | G | H |
| EB conversion wt % | 51.0 | 53.1 | 58.3 | 56.2 | 43.0 | 46.7 | 43.9 | 45.6 |
| PX/XY | 23.2 | 23.5 | 23.7 | 23.7 | 23.3 | 23.1 | 23.2 | 22.8 |
| XY recovery | 95.0 | 95.9 | 95.3 | 95.1 | 95.8 | 97.6 | 96.7 | 97.1 |

TABLE 7

| | | Evaluation of various catalysts | | | | |
|---|---|---|---|---|---|---|
| | Item | | Example 12 | Example 13 | Example 14 | Comparative Example 1 | Comparative Example 2 |
| | Catalyst | | I | J | K | L | M |
| Reaction Conditions | Reaction Temperature (°C.) | | 370 | 370 | 370 | 370 | 370 |
| | Reaction Pressure (kg/cm$^2$ · G) | | 12 | 12 | 12 | 12 | 12 |
| | H$_2$/F (mol/mol) | | 4 | 4 | 4 | 4 | 4 |
| | W/F (g-cat · hr/g-mol) | | 30 | 30 | 30 | 30 | 30 |
| Reaction Products | C$_7^-$ wt. % | (Feed stock) | 1.56 | 2.42 | 2.00 | 1.43 | 0.55 |
| | BZ | | 6.36 | 6.79 | 5.63 | 5.39 | 0.90 |
| | TOL | | 1.16 | 0.97 | 0.65 | 0.68 | 0.97 |
| | EB | 19.06 | 7.25 | 7.95 | 9.95 | 9.02 | 17.11 |
| | PX | 2.66 | 17.66 | 17.63 | 17.64 | 11.37 | 17.46 |
| | MX | 55.48 | 42.15 | 42.33 | 42.54 | 46.58 | 42.60 |
| | OX | 22.80 | 19.08 | 19.35 | 19.51 | 21.80 | 19.42 |
| | ET | | 0.39 | 0.30 | 0.20 | 0.35 | 0.11 |
| | TMB | | 0.51 | 0.41 | 0.37 | 0.01 | 0.56 |
| | DEB | | 2.85 | 1.13 | 1.04 | 2.68 | 0.21 |
| | EX | | 1.03 | 0.71 | 0.46 | 0.70 | 0.11 |
| EB conversion wt % | | | 62.0 | 58.3 | 47.8 | 52.7 | 10.2 |
| PX/XY | | | 22.4 | 22.2 | 22.1 | 14.3 | 22.0 |
| XY recovery | | | 97.5 | 98.0 | 98.5 | 98.5 | 98.2 |

Note
C$_7^-$: non-arcmatic components of C$_1$-C$_7$
BZ: benzene
TOL: toluene
EB: ethylbenzene
XY: xylenes
PX: para-xylene
MX: meta-xylene
OX: ortho-xylene
ET: ethyltoluene
TMB: trimethylbenzene
DEB: diethylbenzene
EX: ethylxylene

What is claimed is:

1. A conversion process for xylenes containing ethylbenzene, characterized in that said xylenes containing ethylbenzene are contacted with a catalyst in the presence of hydrogen, said catalyst comprising an acid type mordenite and an acid type zeolite which exhibits the X-ray diffraction pattern described in Table 1, wherein the weight ratio of said zeolite exhibiting the X-ray diffraction pattern described in Table 1 and said mordenite is in the range of 1% to 50% in terms of a percentage by weight of the former based on the total weight of both said zeolites.

2. A conversion process according to claim 1, wherein the ratio of hydrogen ions in said catalyst is in the range of 30% to 90% in terms of gram ion equivalent based on the total exchangeable cations of both said zeolites.

3. A conversion process according to claim 2, wherein said exchangeable cations of both said zeolites are mainly hydrogen ions and alkaline earth metal ions.

4. A conversion process according to claim 1, wherein said catalyst further contains rhenium, molybdenum, tungsten, vanadium, or a compound thereof.

5. A conversion process according to claim 4, wherein the content of rhenium or a compound thereof is in the range of 0.005 to 3.0 percent by weight as element based on the total weight of said catalyst.

6. A conversion process according to claim 4, wherein the content of molybdenum, tungsten, vanadium, or a compound thereof is in the range of 0.1 to 10 percent by weight as element based on the total weight of said catalyst.

7. A conversion process according to claim 1, wherein said catalyst consists mainly of said mordenite and an acid type zeolite which exhibits the X-ray diffraction pattern described in Table 2.

8. A conversion process according to claim 1, wherein said zeolite exhibiting the X-ray diffraction pattern described in Table 1 is ZSM-5, ZSM-8, ZSM-11, Zeta-3, a zeolite prepared without adding an organic substance into reaction mixture, or a zeolite prepared by adding a carboxyl group-containing organic compound into reaction mixture.

9. A conversion process according to claim 1, wherein the conversion reaction comprises deethylation of ethylbenzene and isomerization of xylenes.

10. A conversion process according to claim 1, wherein the conversion reaction is carried out at a temperature in the range of 300° to 600° C. and at a pressure in the range of atmospheric pressure to 100 kg/cm$^2$.G.

11. A conversion process according to claim 1, wherein the amount of hydrogen is in the range of 1 to 50 moles per mole of said xylenes containing ethylbenzene.

* * * * *